United States Patent [19]
Slishman

[11] Patent Number: 6,161,931
[45] Date of Patent: Dec. 19, 2000

[54] FIBEROPTIC FUNDOSCOPE COUPLER

[75] Inventor: Samuel H. Slishman, Albuquerque, N. Mex.

[73] Assignee: University of New Mexico, Albuquerque, N. Mex.

[21] Appl. No.: 09/330,986

[22] Filed: Jun. 14, 1999

[51] Int. Cl.[7] ...................................................... A61B 3/00
[52] U.S. Cl. ............................................................. 351/200
[58] Field of Search .................................... 351/200, 205, 351/221, 160 R; 600/489, 109; 348/359; 606/5, 166

[56] References Cited

U.S. PATENT DOCUMENTS

| | | | |
|---|---|---|---|
| 3,706,304 | 12/1972 | Sisler | 600/489 |
| 3,770,342 | 11/1973 | Dudragne . | |
| 3,903,871 | 9/1975 | Chisum et al. | 600/489 |
| 3,929,124 | 12/1975 | Yablonski et al. | 600/489 |
| 4,259,948 | 4/1981 | Urban | 600/109 |
| 4,796,623 | 1/1989 | Krasner et al. | 606/166 |
| 4,856,513 | 8/1989 | Muller | 606/5 |
| 4,941,093 | 7/1990 | Marshall et al. | 606/5 |
| 5,255,025 | 10/1993 | Volk . | |
| 5,336,215 | 8/1994 | Hsueh et al. . | |
| 5,695,492 | 12/1997 | Brown . | |

*Primary Examiner*—George Manuel
*Attorney, Agent, or Firm*—Jagtiani & Associates

[57] ABSTRACT

The present invention provides a coupler device that can be adhered by suction to an examination object to facilitate observation. The present invention also provides a method for observing an examination object comprising the steps of placing a coupler device in contact with an examination object, applying suction to adhere the coupler device to the examination object, and observing the examination object.

12 Claims, 2 Drawing Sheets

FIBEROPTIC FUNDOSCOPE COUPLER

BACKGROUND OF THE INVENTION

1. Field of the Invention

The present invention relates generally to devices utilized to observe the eye.

2. Description of the Prior Art

Methods of examining cavities involving steps of illuminating the area to be observed are known. For example, oblique illumination of the eye during examination has been demonstrated in U.S. Pat. No. 5,695,492 to Brown. However, this method of illumination does not provide a direct path of light into the area being observed. One solution to this problem might be to provide axial illumination of the eye. However, it is further noted in Brown that intense axial illumination of the eye can result in patient discomfort, and this patient discomfort can result in an inability to maintain a steady gaze by the patient during observation.

SUMMARY OF THE INVENTION

Therefore, it is an object of the present invention to provide an improved eye illumination apparatus which allows for improved visualization of the fundus of the eye and other internal structures.

It is a further object of the present invention to provide a device for direct ophthalmoscopy that axially illuminates an eye while allowing for eye movement during continuous observation.

It is yet a further object of the present invention to provide a fiberoptic funduscope coupler that adheres to and furnishes axial illumination into an eye. The eye, thus illuminated, may be observed even while the eye or the observer is moving.

According to one aspect of the present invention, there is provided a device for observing an examination object, comprising a substantially cup shaped body and a means for applying suction to detachably adhere the cup shaped body to an examination object.

According to a second aspect of the invention there is provided a method for observing an examination object comprising the steps of placing a device in contact with an examination object, applying suction to the device to maintain contact between the device and the examination object, and observing the examination object using the device.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

Definitions

Figure 2:
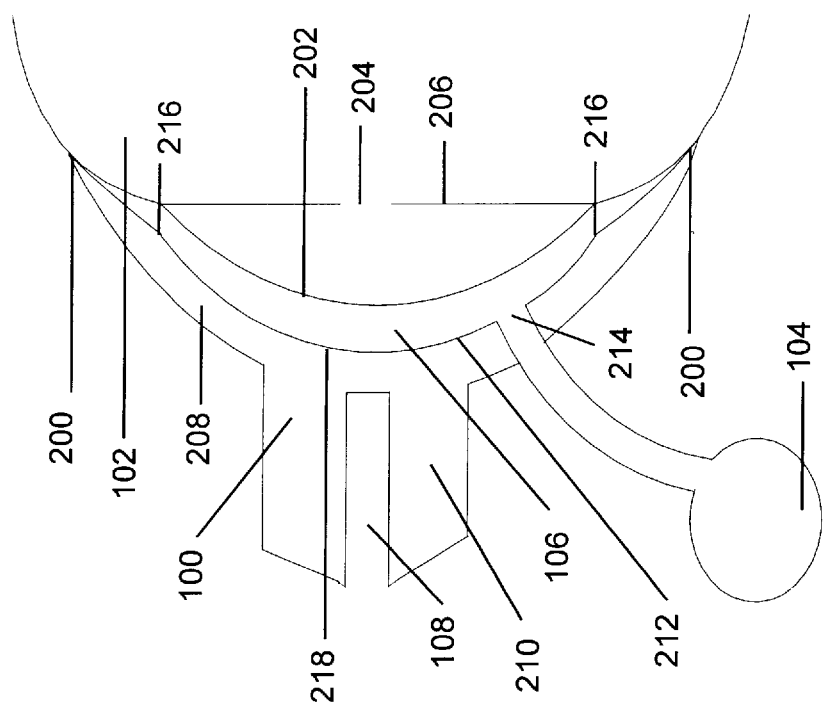
FIG. 2 is a cross-sectional side view in schematic form of the fiberoptic funduscope coupler of FIG. 1 that shows the coupler in greater detail.

For the purposes of the present invention, the term "examination object" refers to an item to be observed through use of the device of the present invention or by using the method of the present invention. The object is preferably an eye, but may be another body part, or even an inanimate object.

For the purposes of the present invention, the term "observation tool" refers to a device that facilitates observation. An observation tool is used to transmit and view an object or image, and may have a means for adjusting, enlarging, or focusing the image of the object for viewing by the person making the examination. Further, the observation tool of the present invention may be flexible to allow for motion by the person making the examination, the examination object, or both. The observation tool of the present invention is preferably sized to be readily transportable and held with one hand. One example of an examination tool is an ophthalmoscope, but other suitable examination tools include an endoscope, otoscope, etc.

For the purposes of the present invention, the term "relaxed state" refers to the state when the device of the present invention is in contact with the examination object but suction has not been applied.

For the purposes of the present invention, the term "operational state" refers to the state when suction has been applied to adhere the device to an examination object.

The device of the present invention is operational while in the relaxed state but it is preferable to employ suction prior to use.

For the purposes of the present invention, the term "proximal" refers to the portion of an examination tool or cup shaped body nearest to the person using the tool or cup shape body to make an examination.

For the purposes of the present invention the term "distal" refers to the portion of an examination tool or cup shaped body furthest from the person using the tool or cup shaped body to make an examination.

For the purposes of the present invention the phrase "using the device" refers to using the funduscope device of the present invention in some way to make an observation, such as illuminating an object to be observed or viewing an object through the device.

For the purposes of the present invention, the phrase "axially illuminating" refers to introducing illumination in a direction substantially perpendicular to the surface of the examination object being observed.

Description

Traditionally, direct or indirect ophthalmoscopy has only required a relatively stable eye for examination. Cooperative patients must maintain a fixed gaze of sufficient steadiness to accomplish examination. Due to a lack of a steady gaze the eye of an uncooperative or incompetent patient is difficult to examine through direct or indirect ophthalmoscopy. The present invention provides a means to continuously contact the eye during examination, and allows direct ophthalmoscopy to be more readily performed on an uncooperative or incompetent patient's eye.

Eye surgery is extremely precise and requires stabilization of the eye. This stabilization can be accomplished through a mechanical link in which the equipment comprising the surgical apparatus incorporates a mechanism that contacts the eye and holds it stable. Suction may be the means to stabilize the eye, as described in U.S. Pat. No. 5,336,215 to Hsueh, et. al. However, the use of suction to stabilize the eye of a patient for direct ophthalmoscopy has not been used. To examine an eye using the coupler device of the present invention, complete stabilization of the eye is not necessary, since the coupler device fixes the examination tool to the roving eye and does not need to curtail movement of the eye for proper examination.

Figure 1:
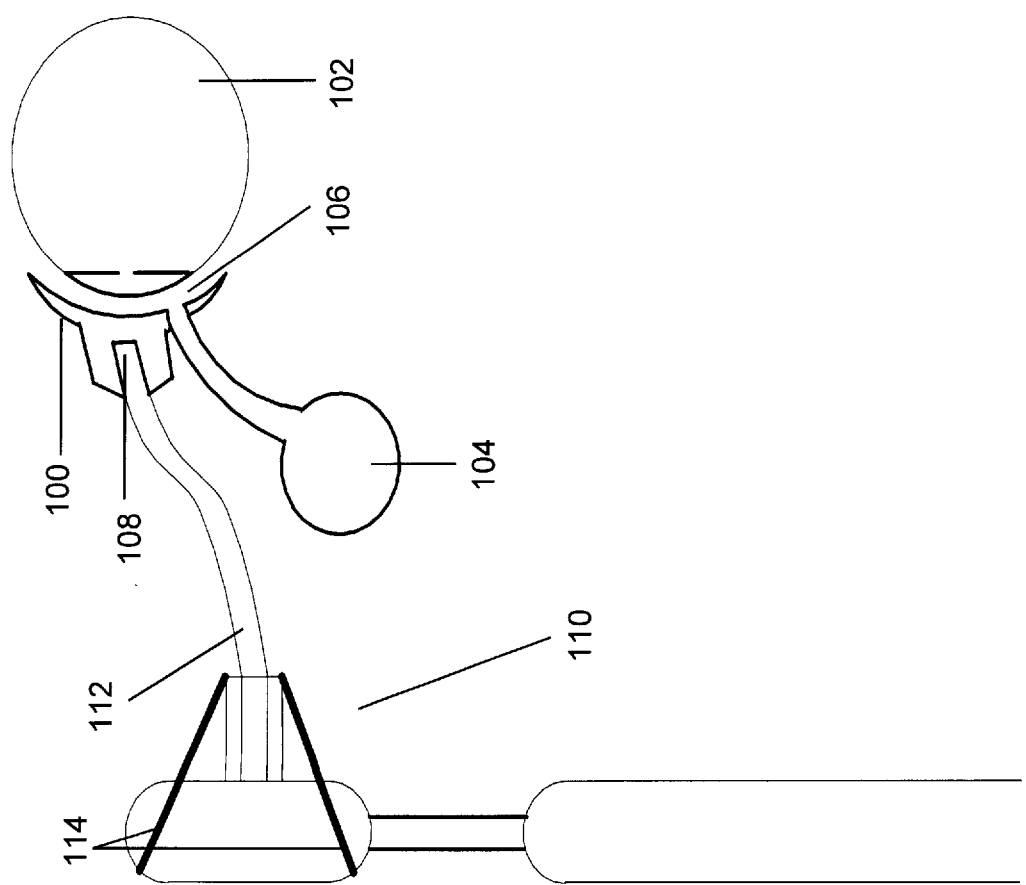
FIG. 1 is a cross-sectional side view in schematic form of an embodiment of a fiberoptic funduscope coupler with an observation tool made according to the present invention.

FIG. 1 illustrates a preferred embodiment of a cup shaped fiberoptic funduscope coupler device 100 made according to the present invention. Coupler device 100 is connected to an examination tool 110 at an attachment site 108. Attachment site 108 is located on the proximal surface of coupler device 100 and serves as a location to engage a fiberoptic cable 112. Coupler device 100 may be made from any material suitable for a conventional contact lens, as well as other flexible materials that are sufficiently gentle corresponding to the delicacy of eye 102.

Although a fiberoptic cable is shown attached to the attachment site in the embodiment of the present invention shown in FIG. 1, other examination tools and components, such as a video transmitter, may be attached to the attachment site. Use of a video transmitter would allow for viewing of the image by a person not in the immediate vicinity of examination object. This may be desirable when examination object is highly infectious, when a person of special diagnostic capabilities is not located in the vicinity of the examination object, or for teaching purposes.

Examination tool 110 may be used to stabilize the proximal end of coupler device 100 during an examination. Tool 110 may be an ophthalmoscope or other medical device. As shown in the embodiment of FIG. 1, tool 110 includes detachable elastic straps 114 that engage fiberoptic cable 112. In embodiments of the present invention where the examination tool and fiberoptic cable are permanently joined, the elastic straps may be omitted. Elastic straps 114 may also be replaced with another suitable attachment means where desirable.

Fiberoptic cable 112 may be permanently attached to either coupler device 100, tool 110, both, or neither. Fiberoptic cable 112 may be rigid or flexible, depending on the materials selected for its construction. The intensity of illumination may be controlled at the source or by selective use of materials in fiberoptic cable 112.

In FIG. 1 coupler device 100 is depicted in a relaxed state adjacent to but not touching an examination object, a human eye 102. A gap 106 exists between coupler device 100 and eye 102 at all points while coupler device 100 is in a relaxed state. Coupler device 100 also includes a suction device 104 that is used to detachably adhere coupler device 100 to eye 102.

Although FIG. 1 shows an embodiment of the coupler device of the present invention that is used to examine a human eye, the coupler device of the present invention may also be used to examine body parts and even inanimate objects.

FIG. 2 is an enlarged view of cup shaped fiberoptic funduscope coupler device 100. For simplicity, not all of the features of coupler device 100 are depicted or labeled in all of the drawing figures depicting coupler device 100. Coupler device 100 is shown with a vacant attachment site 108 on the proximal side 210 of coupler device 100. The attachment site of the present invention may be any one of a variety of shapes and sizes depending on what type of examination tool is to be attached. Attachment site 108 may be permanently fixed to coupler device 100 or detachable. Also, the connection between attachment site 108 and fiberoptic cable 112 may be permanent or detachable. As shown in FIG. 2, coupler device 100 is centered on pupil 204 and covers iris 206 when coupler device 100 is placed on eye 102 in a relaxed state.

As shown in FIG. 2, suction device 104 is a squeezable bulb in communication with gap 106 through an aperture 214. The suction device of the present invention may be a bulb suction device as shown or other type of suction device. When the suction device is a bulb suction device, the device is a generally spherical object made of a deformable material such as rubber, plastic, etc. Aperture 214 allows air trapped in gap 106 to be drawn into suction device 104, thereby forcing distal surface 212 closer to eye 102. Another type of suction device is a vacuum.

Figure 3:
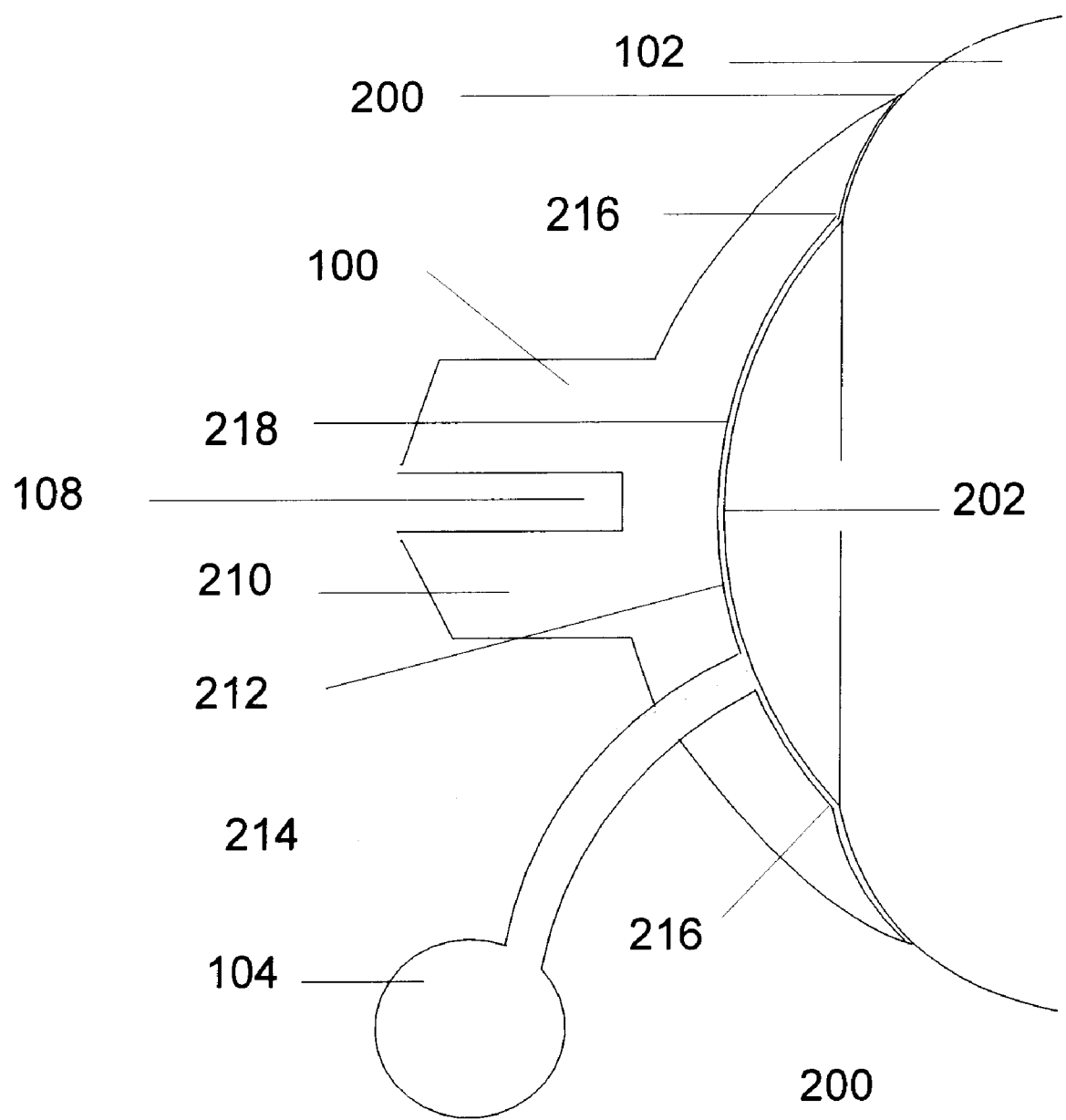
FIG. 3 is a cross-sectional side view in schematic form of the fiberoptic funduscope coupler of FIG. 2 that shows the coupler in a position adjacent to the eye.

Also, as shown in FIG. 2, coupler device 100 includes a cup shaped portion 208. Cup shaped portion 208 has a primary corneal engagement site 216 denoting the area of cup shaped portion 208 that first contacts the cornea 202 when the coupler device is in an operational state, as shown in FIG. 3. Primary corneal engagement site 216 has a greater curvature than the central portion 218 to better fit on the surface of eye 102. As distal surface 212 of coupler device 100 moves closer to the eye 102 and specifically to cornea 202, the degree of curvature in the central portion 218 of cup shaped portion 208 increases while the degree of curvature in cup shaped portion 208 near contact point 200 remains relatively the same.

FIG. 3 shows cup shaped fiberoptic funduscope coupler device 100 in an operational state. Suction device 104 has been employed to remove air from gap 106 (not present in FIG. 3) and coupler device 100 is held adjacent to eye 102. The shape of distal surface 212 preferably corresponds to the shape of eye 102 as closely as possible. For example, central portion 218 preferably replicates the proximal bulge of cornea 202.

Because coupler device 100 allows for direct contact and the application of suction to the eye 102, there may be limits on the duration of time that coupler device 100 may be in contact with eye 102. It is generally preferable to discontinue use of coupler device 100 within minutes to reduce the possibility of damage to eye 102. When the coupler device of the present invention is used to examine an eye, preferably the attachment site is located so that the end of the fiberoptic cable is as close as possible to the pupil after suction is applied.

Due to the variation in sizes of eyes and degrees of curvature of corneas throughout life and among patients, it may be preferable to make the coupler device of the present invention detachable from the fiberoptic cable or to make the coupler device and fliberoptic cable detachable from the examination tool. In this way, coupler devices of various sizes and shapes may be used with a given fiberoptic cable attached to an examination tool or with a given examination tool.

Also, given the tender nature of the eye and the ease of communication of disease into the eye, it may be preferable to utilize disposable materials in making the coupler device to reduce the risk of disease transmission between uses. Further, given the delicate nature of some of the materials that are acceptable for use in the coupler device, it may be preferable to provide permanent attachment between the examination tool and the coupler device at the attachment site for the coupler device. This arrangement may reduce the likelihood of severe damage to the eye caused by improper insertion of the tool.

Although a particular embodiment of the coupler device of the present invention is shown in FIGS. 1 through 3, it should be understood that the present invention encompasses many arrangements of coupler devices. For example, the flexible fiberoptic cable shown in FIGS. 1 through 3, may be replaced by a rigid viewing tube or other instrument. Also, it may be desirable to for certain medical instruments to be placed directly on the surface of the coupler device without the intervention of a fiberoptic cable. In addition, as mentioned previously, a video transmitter may be placed in the coupler device to allow for remote viewing of the eye.

Also, although the present invention has been describe for use in examining an individual's eye, the coupler device of the present invention may be used to examine other body parts or even inanimate objects. For example, by using an appropriately shaped coupler device, a portion of a human lung or major artery may be examined using the coupler device of the present invention.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A device for observing an examination object, comprising:
    a substantially cup shaped body including a lens region for being mounted in contact with an examination object and for allowing light to be transmitted through said substantially cup shaped body;
    a means for applying suction to detachably adhere said substantially cup shaped body to the examination object with which said lens region is mounted in contact; and
    an attachment means on said substantially cup shaped body for mounting an observation tool so as to be in contact with said lens region.

2. The device of claim 1, wherein:
    said suction means comprises a hollow bulb in communication through an aperture through said cup shaped body with a gap created when said device is placed against the examination object when said device is in a relaxed state.

3. The device of claim 1, further comprising:
    an observation tool attached to and extending proximally from said cup shaped body and being in contact with said lens region.

4. The device of claim 3, wherein:
    said observation tool is detachably connected to said substantially cup shaped body.

5. The device of claim 3, wherein:
    said observation tool is fixedly connected to said substantially cup shaped body.

6. The device of claim 3, wherein:
    said observation tool comprises a fiberoptic cable.

7. The device of claim 1, wherein:
    said substantially cup shaped body is shaped to engage at least a portion of an eye.

8. The device of claim 1, wherein:
    said substantially cup shaped body is shaped to engage the cornea of an eye.

9. A method for observing an examination object, comprising the steps of:
    placing a substantially cup shaped device on an examination object so that a lens region of said cup shaped device is in contact with the examination object;
    applying suction to said device to maintain constant contact between said lens region and said examination object; and
    observing said examination object through said lens region of said substantially cup shaped device using an observation tool attached to and in contact with said lens region.

10. The method of claim 9, wherein:
    said examination object is an eye.

11. The method of claim 9, further comprising the step of:
    axially illuminating said examination object through said observation tool attached to said substantially cup shaped device.

12. The method of claim 9, wherein:
    said observation tool comprises an ophthalmoscope.

* * * * *